US011352437B2

(12) United States Patent
Beaudoin et al.

(10) Patent No.: US 11,352,437 B2
(45) Date of Patent: Jun. 7, 2022

(54) CONJUGATES ENHANCING TOTAL CELLULAR ACCUMULATION

(71) Applicant: DEFENCE THERAPEUTICS INC., Vancouver (CA)

(72) Inventors: Simon Beaudoin, Sherbrooke (CA); Jeffrey Victor Leyton, Sherbrooke (CA)

(73) Assignee: DEFENCE THERAPEUTICS INC., Vancouver (CA)

( * ) Notice: Subject to any disclaimer, the term of this patent is extended or adjusted under 35 U.S.C. 154(b) by 0 days.

(21) Appl. No.: 16/085,141

(22) PCT Filed: Mar. 15, 2017

(86) PCT No.: PCT/CA2017/050337
§ 371 (c)(1),
(2) Date: Sep. 14, 2018

(87) PCT Pub. No.: WO2017/156630
PCT Pub. Date: Sep. 21, 2017

(65) Prior Publication Data
US 2019/0077879 A1    Mar. 14, 2019

Related U.S. Application Data

(60) Provisional application No. 62/308,457, filed on Mar. 15, 2016.

(51) Int. Cl.
| | |
|---|---|
| *A61K 47/64* | (2017.01) |
| *A61K 47/68* | (2017.01) |
| *C07K 16/32* | (2006.01) |
| *C07K 16/30* | (2006.01) |
| *C12N 15/11* | (2006.01) |
| *A61K 47/54* | (2017.01) |
| *C07J 9/00* | (2006.01) |

(52) U.S. Cl.
CPC ............ *C07K 16/32* (2013.01); *A61K 47/542* (2017.08); *A61K 47/64* (2017.08); *A61K 47/6803* (2017.08); *A61K 47/6845* (2017.08); *A61K 47/6855* (2017.08); *C07K 16/3061* (2013.01); *C12N 15/111* (2013.01); *C07J 9/005* (2013.01); *C07K 2317/77* (2013.01); *C07K 2319/09* (2013.01); *C07K 2319/55* (2013.01); *C12N 2310/11* (2013.01); *C12N 2310/14* (2013.01); *C12N 2310/3513* (2013.01); *C12N 2310/3515* (2013.01); *C12N 2320/32* (2013.01); *C12N 2710/22022* (2013.01)

(58) Field of Classification Search
CPC .............. A61K 47/00; A61K 47/6855; A61K 47/6845; A61K 47/6803; A61K 47/64; A61K 47/542; A61K 2123/00; A61K 2121/00; C07K 16/32; C07K 16/3061; C07K 2319/55; C07K 2319/09; C07K 2317/77; C12N 15/111; C12N 2320/32; C12N 2310/3515; C12N 2310/14; C12N 2310/11; C12N 2310/3513; C12N 2710/22022; C07J 9/005
USPC .......... 424/1.11, 1.49, 1.65, 1.69, 1.81, 1.85, 424/1.89, 9.1, 9.2, 9.3, 9.4, 9.5, 9.6; 514/1, 1.1, 19.2, 19.3, 19.4, 19.5, 19.6; 530/300; 534/7, 10–16
See application file for complete search history.

(56) References Cited

U.S. PATENT DOCUMENTS

| | | | | |
|---|---|---|---|---|
| 5,955,365 A | * | 9/1999 | Szoka, Jr. | ............... A61P 19/00 435/441 |
| 7,732,177 B2 | * | 6/2010 | Iadonato | .............. C12N 9/1241 435/189 |

OTHER PUBLICATIONS

Swaan et al, Bioconjugate Chemistry, vol. 8, pp. 520-525. (Year: 1997).*
Leyton et al, J. Nucl. Med., vol. 52, No. 9, pp. 1465-1473. (Year: 2011).*
Cokol et al, EMBO Reports, vol. 1, No. 5, pp. 411-415 (Year: 2000).*
Beaudoin et al, Mol. Pharmaceutics, vol. 13, pp. 1915-1926 (Year: 2016).*
Beaudoin et al. "ChAcNLS, a Novel Modification to Antibody-Conjugates Permitting Target Cell-Specific Endosomal Escape, Localization to the Nucleus, and Enhanced Total Intracellular Accumulation." Molecular Pharmaceutics, vol. 13, 1915-1926, 2016.
Leyton er al. "Auger Electron Radioimmunotherapeutic Agent Specific for the CD123+/CD131-Phenotype of the Leukemia Stem Cell Population." The Journal of Nuclear Medicine, vol. 52, No. 9, 1465-1473, 2011.
Swaan et al. "Enhanced Transepithelial Transport of Peptides by Conjugation to Cholic Acid", Bioconjugate Chemistry, vol. 8, No. 4, 520-525, 1997.
Raouane et al. "Lipid Conjugated Oligonucleotides: A Useful Strategy for Delivery", Bioconjugate Chemisrty, vol. 23, pp. 1091-1104, 2012.
Manoharan et al. "Cholic Acid-Oligonucleotide Conjugates for Antisense Applications", Bioorganic and Medicinal Chemistry Letter, vol. 4, No. 8, 1053-1060, 1994.
Kim Bieong-Kil et al. "Homodimeric SV40 NLS peptide formed by disulfide bond as enhancer for gene delivery", Bioorganic & Medicinal chemistry letters, vol. 22, No. 17, 2020, pp. 5415-5418.
Lacasse et al., "A novel and generalizable proteomic method reveals classical NLS-tagging of trastuzumab-emtansine contravenes classical nuclear transport in a model of HER2-positive breast cancer" Molecular Therapy: Methods & Clinical Development (2020) doi: https://doi.org/10.1016/j.omtm.2020.08.016.

(Continued)

Primary Examiner — D. L. Jones
(74) Attorney, Agent, or Firm — Norton Rose Fulbright Canada LLP (57) ABSTRACT

The present description relates to a conjugated compound comprising cholic acid (ChAc) or a variant thereof, the ChAc conjugated to a non-cell penetrating peptide comprising a nuclear localization sequence (NLS) conjugated to a compound of interest.

14 Claims, 10 Drawing Sheets

Specification includes a Sequence Listing.

(56) References Cited

OTHER PUBLICATIONS

Beaudoin et al. "ChAcNLS, a Novel Modification to Antibody-Conjugates Permitting Target Cell-Specific Endosomal Escape, Localization to the Nucleus, and Enhanced Total Intracellular Accumulation" Mol. pharmaceutics, 2016, 13, 1915-1926.

Murakami et al. "Bile acids and ceramide overcome the entry restriction for GII.3 human norovirus replication in human intestinal enteroids", PNAS, 2020, vol. 117, No. 3, 1700-1710.

Sun et al. "Factors influencing the nuclear targeting ability of nuclear localization signals", Journal of drug targeting, 2016, vol. 24, No. 14, 927-933.

Lam and Dean, "Progress and prospects: nuclear import of nonviral vectors", Gene Therapy, 2010, 17, 439-447.

Sun et al. "Factors influencing the nuclear targeting ability of nuclear localization signals", Journal of Drug Targeting, 24:10, 927-933 (2016).

Kim et al. "The molecular mechanism for nuclear transport and its application", Anat Cell Biol 2017;50:77-85.

Kosugi et al. "Six Classes of Nuclear Localization Signals Specific to Different Binding Grooves of Importin", J. Biol. Chem. 2009, 284:478-485.

Kenney et al. "Identification and Fine Mapping of Nuclear and Nucleolar Localization Signals within the Human Ribosomal Protein S17", Protein S17. PLoS ONE 10(4): e0124396.

Tomatsidou et al. "Evaluation of peptide-mediated nucleic acid delivery", Department of Pharmaceutics, Utrecht Institute of Pharmaceutical Sciences (UIPS), Utrecht University, 2013, pp. 1-33.

Chugh et al. "Cell-Penetrating Peptides: Nanocarrier for Macromolecule Delivery in Living Cells", IUBMB Life, 62(3): 183-193, Mar. 2010.

Ray et al. "Quantitative tracking of protein trafficking to the nucleus using cytosolic protein delivery by nanoparticle-stabilized nanocapsules" Bioconjug Chem. Jun. 17, 2015; 26(6): 1004-1007. doi:10.1021/acs.bioconjchem.5b00141.

Shivanna et al. "The crucial role of bile acids in the entry of porcine enteric calicivirus", Virology 456-457 (2014) 268-278.

Chang et al. "Bile acids are essential for porcine enteric calicivirus replication in association with down-regulation of signal transducer and activator of transcription 1", PNAS, 2004, vol. 101, No. 23.

\* cited by examiner

CONJUGATES ENHANCING TOTAL CELLULAR ACCUMULATION

CROSS-REFERENCE TO RELATED APPLICATIONS

This application is a U.S. National Phase of International Application No. PCT/CA2017/050337, filed on Mar. 15, 2017 and claiming priority from U.S. provisional patent application 62/308,457 filed on Mar. 15, 2016, and this application claims priority to and the benefit of the above-identified applications, each of which are incorporated by reference herewith in their entirety.

TECHNICAL FIELD

The present relates to a conjugate compound that enhances total intracellular accumulation.

BACKGROUND ART

The design of antibody-conjugates (ACs) for delivering molecules for therapy or imaging applications in humans has sufficiently progressed to demonstrate clinical efficacy in certain malignancies and reduce systemic toxicity that occurs with standard chemotherapy or radiation.

ACs have demonstrated success to deliver payloads of drugs selectively against cancer cells for therapeutic or imaging applications in humans. However, AC technology, whether in the form of antibodies armed with radioactive isotopes or cytotoxic drugs, is still looking to develop into more effective and widely applicable pharmaceuticals for improved and more widespread cancer management.

The universal cornerstone for intracellular drug accumulation by antibody-drug conjugates (ADCs) is reliant on its cellular internalization pathway. Once bound to target antigen, ADCs are internalized and entrapped inside endosomes and trafficked to the lysosome. Lysosomes are membrane-enclosed organelles that contain an array of digestive enzymes and receive proteins transported by endosomes through vesicle membrane fusion and results in the release of active drug catabolites. The intracellular accumulation of these catabolites is directly correlated with cytotoxic potency. This dependency is what currently plagues ADCs and prevents them from achieving their full potential. Cancer cells respond to ADCs by increasing the expression of drug efflux pumps and decreasing the expression of target receptors. Receptor recycling pathways and their increased used by cancer cells has also been implicated to reduce the intracellular accumulation of the internalized ADCs. In essence, the field has long relied on an inefficient process for intracellular accumulation and there is no research directly addressing this problem. Therefore, avoiding entrapment in these intracellular pathways is an important area to improve the cellular accumulation of transported drugs and for maximizing ADC activity.

The functionalization of monoclonal antibodies (mAbs) with cell-penetrating peptides has resulted in remarkable increases in intracellular accumulation when cells are treated with these types of ACs. However, this advancement in AC cellular accumulation has been mostly for allowing mAbs to access and target specific molecules inside cells that would otherwise be unavailable for antibodies to target. Of the few reports that attempt to utilize ACs equipped with cell-penetrating peptides as therapeutic agents against cell surface cancer-specific receptors, all suffered from high accumulation in non-target cells or tissues and thus are limited in their application for targeted delivery.

Recent advancements whereby ACs functionalized with pH-sensitive polymers have shown impressive abilities to escape endosomes and enter the cytoplasm while maintaining target cell selectivity. However, it is yet to be determined whether increased escape by these ACs corresponds to an increase in intracellular accumulation.

Another recent advancement has been to empower ACs to achieve multi-selective targeting by attaching peptides that harbor compartment-localizing amino acids. In particular, the nuclear localization signal (NLS) sequence from SV-40 Large T-antigen has previously been incorporated into synthetic peptides and conjugated to proteins and demonstrated the ability to direct the transport of proteins into the nucleus. Although, the optimized NLS sequence is 25 amino acids long, the mAb 7G3 was conjugated to a 13-mer peptide (CGYGPKKKRKVGG) harboring a segment of the NLS (underlined) sufficient for nuclear translocation. An advantage of this short sequence is that it does not penetrate cells and allows mAbs to maintain cell selectivity. 7G3-NLS was used to deliver the radioisotope cargo indium-111 ($^{111}$In) inside the nucleus. Molecular damage by $^{111}$In is due to its emissions of energetic Auger electrons. Because they travel only nanometer-micrometer distances they are more effective if delivered inside the nucleus. Unfortunately, cytotoxicity was not overwhelming relative to standard $^{111}$In-7G3 and the evidence suggested it was due to ineffective nuclear localization caused by entrapment in the endosomal-lysosomal and/or recycling pathways.

Therefore, there is still a need to be provided with an AC that is effective in circumventing the entrapment of the endosomal-lysosomal and/or recycling pathways.

SUMMARY

In accordance with the present description, there is now provided a conjugated compound comprising cholic acid (ChAc) or a variant thereof, the ChAc conjugated to a non-cell penetrating peptide comprising a nuclear localization sequence (NLS) conjugated to a compound of interest.

In an embodiment, the compound of interest is an antibody, a small molecule, an oligonucleotide, an antisense, a drug or a siRNA molecule.

In another embodiment, the antibody is a monoclonal or polyclonal antibody.

In a further embodiment, the antibody is a mouse antibody, a goat antibody, a human antibody or a rabbit antibody.

In an embodiment, the antibody is a humanized antibody.

In another embodiment, the antibody comprises an epitope binding fragment selected from the group consisting of: Fv, F(ab') and F(ab')$_2$.

In a further embodiment, the nuclear localization sequence is from SV40 large T antigen.

In another embodiment, the non-cell penetrating peptide comprises at least one spacer residue.

In an additional embodiment, the non-cell penetrating peptide comprises at least one cysteine for coupling to ChAc and the compound of interest.

In a further embodiment, the non-cell penetrating peptide is as set forth in SEQ ID NO:1.

In another embodiment, the compound of interest is the 7G3 antibody or the 6G7 antibody.

In a further embodiment, the ratio of ChAcNLS peptide conjugated per compound of interest is between 1 to 21 peptides per compound.

In another embodiment, the conjugated compound described herein further comprises a radionuclide attached thereto.

In an embodiment, the radionuclide is at least one of $^{47}$Sc, $^{51}$Cr, $^{52m}$Mn, $^{55}$Co, $^{58}$Co, $^{52}$Fe $^{56}$Ni, $^{57}$Ni, $^{61}$Cu, $^{62}$Cu, $^{64}$Cu, $^{67}$Cu, $^{66}$Ga, $^{68}$Ga, $^{67}$Ga $^{72}$As, $^{77}$As, $^{89}$Zr, $^{90}$Y, $^{94m}$Tc, $^{99m}$Tc, $^{97}$Ru, $^{105}$Rh, $^{109}$Pd, $^{111}$Ag, $^{110}$In, $^{111}$In, $^{113}$min, $^{114}$min, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi, $^{213}$Bi, $^{11}$C, $^{75}$Br, $^{76}$Br, $^{77}$Br, $^{82}$Br, $^{18}$F, $^{120}$I, $^{123}$I, $^{124}$I, $^{125}$I, $^{131}$I, $^{89}$Sr and $^{225}$Ac.

In a further embodiment, the radionuclide is $^{64}$Cu.

In another embodiment, the conjugated compound described herein further comprises a small molecule toxin attached thereto.

In an embodiment, the small molecule toxin is a chemotherapeutic agent.

In another embodiment, the small molecule toxin is a microtubule disrupting agent or a DNA alkylating agent.

In a further embodiment, the small molecule toxin is vinblastine, emtansine, Monomethyl auristatin E or 4,4-difluoro-8-(4-carboxyphenyl)-1,3,5,7-tetramethyl-4-bora-3a,4a-diaza-s-indacene (BODIPY).

In an additional embodiment, the conjugated compound described herein is for detecting prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

In an embodiment, the conjugated compound described herein is for treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is also provided herein of the use of the conjugated compound as described herein for treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is further provided the use of the conjugated compound as described herein in the manufacture of a medicament for treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is additionally provided herein the use of the conjugated compound as described herein for detecting prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is also provided a method of treating and/or detecting prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis in a subject comprising administering to said subject the conjugated compound as described herein.

In an embodiment, the subject is a human or a mouse.

BRIEF DESCRIPTION OF THE DRAWINGS

Reference will now be made to the accompanying drawings.

DETAILED DESCRIPTION

It is provided a novel design of compound-conjugates specific against rapidly internalizing receptors to link endosome escape and enhanced cellular uptake. More specifically, it is provided a conjugated compound comprising cholic acid conjugated to a non-cell penetrating peptide comprising a nuclear localization sequence (NLS) conjugated to the compound of interest.

As demonstrated herein, it is provided for example a conjugated compound that escape from entrapment inside the endosome-lysosome system followed by translocation to the nucleus, and increase for example accumulation of the compound inside targeted IL-3Rα$^+$TF-1a leukemia cells.

Example of conjugated compounds include, and not limited to, an antibody, an oligonucleotide, an antisense, a drug, or an siRNA molecule, and not excluded are any small molecule or biological for which it has an intracellular target, that cannot penetrate mammalian membranes.

In an embodiment, the antibody is a monoclonal or polyclonal antibody.

In another embodiment, the antibody is a mouse antibody, a goat antibody, a human antibody or a rabbit antibody, or a humanized antibody.

Also encompassed, the antibody might comprises an epitope binding fragment such as for example Fv, F(ab'), and/or F(ab')$_2$.

The 13-mer peptide (CGYGPKKKRKVGG; SEQ ID NO: 1)

that is non-cell penetrating and harbors a segment of the classical NLS (underlined) from SV-40 large T-antigen has been conjugated previously to the anti-CD123 (IL-3Rα) antibody (7G3) and its chimeric version (CSL360) (Leyton et al., 2011, J Nucl Med, 52: 1465-1473). NLS-7G3 and NLS-CSL360 transporting conjugated indium-111 ($^{111}$In) were used to evaluate for their ability to route to the nucleus. Eventhough the presence of the NLS sequence, the proportion of radioactivity delivered in the nucleus was very low whereas the majority of the radioactivity remained on the cell surface or in the cytoplasm (Zerashkian et al., 2014, Nucl Med Biol, 41: 377-383). Thus $^{111}$In-NLSCSL360 remained trapped within the endosome.

One of the antibody used herein, but not limiting the present disclosure, the 7G3 antibody, binds to the IL-3R α-chain and completely abolishes its function. It has been described that the 7G3 antibody can be used for treating myeloid leukaemia, lymphomas such as follicular B cell lymphomas, or the alleviation of allergies (WO 1997/024373).

It is provided herein the addition of cholic acid (ChAc) which was coupled to the peptide CGYGPKKKRKVGG (SEQ ID NO:1) containing a segment of the nuclear localization sequence (NLS) from SV40 large T antigen (ChAcNLS). In an embodiment, the anti-IL-3Rα monoclonal antibody (mAb) 7G3 was functionalized by conjugation to ChAcNLS. In vitro and/or in vivo studies in liquid and solid tumor models were performed to demonstrate that the ChAcNLS technology attached to various molecular cargo such as an antibody can enhance cellular and tumor retention relative to similar modified Abs that lack the ChAc component.

Accordingly, it is provided an antibody, such as for example the 7G3 in a leukemia system, but not limited to, or a small molecule conjugated as described herein Also encompassed herein, but not limited, are radionuclide conjugated to the compound described herein selected from $^{47}$Sc, $^{51}$Cr, $^{52m}$Mn, $^{55}$Co, $^{58}$Co, $^{52}$Fe $^{56}$Ni, $^{57}$Ni, $^{61}$Cu, $^{62}$Cu, $^{64}$Cu, $^{67}$Cu, $^{66}$Ga, $^{68}$Ga, $^{67}$Ga $^{72}$As, $^{77}$As, $^{89}$Zr, $^{90}$Y, $^{94m}$Tc, $^{99m}$Tc, $^{97}$Ru, $^{105}$Rh, $^{109}$Pd, $^{111}$Ag, $^{110}$In, $^{111}$In, $^{113}$min, $^{114}$min, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi, $^{213}$Bi, $^{11}$C, $^{75}$Br, $^{76}$Br, $^{77}$Br, $^{82}$Br, $^{18}$F, $^{120}$I, $^{123}$I, $^{124}$I, $^{125}$I, $^{131}$I, $^{89}$Sr and $^{225}$Ac. In addition, also encompassed are a chemotherapeutic conjugated as described herein, as for example vinblastine.

Figure 1A:
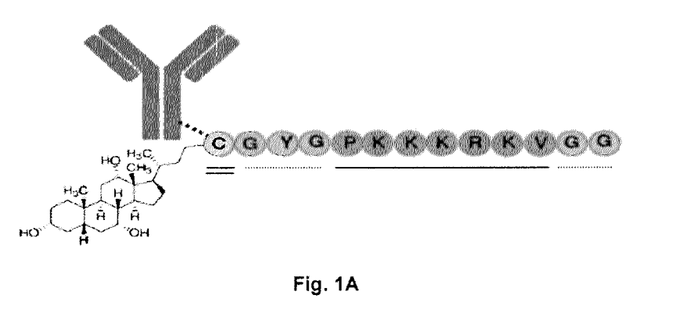
FIG. 1A illustrates a schematic representation of ChAcNLS-7G3 according to one embodiment, wherein residues underlined (—) correspond to the nuclear localization sequence NLS, spacer residues are underlined in (—) and the cysteine (=) used for coupling to ChAc and 7G3 is also shown.
Figure 1B:
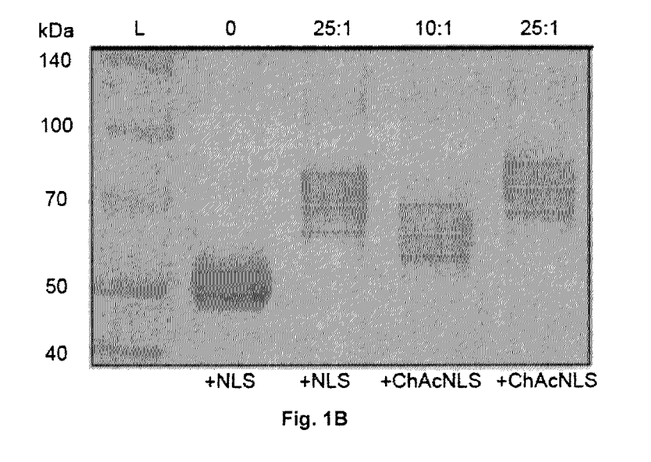
FIG. 1B illustrates a protein band mobility shifts by SDS-PAGE showing the number of peptides per antibody.
Figure 5:
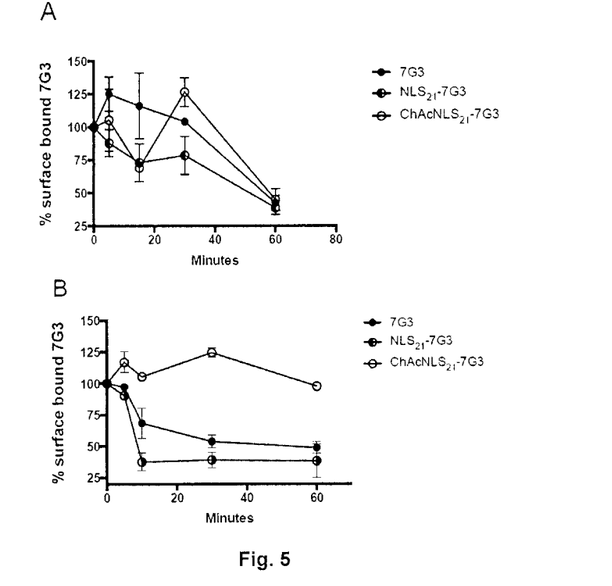
FIG. 5 illustrates ChAcNLS-7G3 internalization, wherein in (A) the % of surface bound 7G3 after TF-1a cells are incubated with 7G3, NLS21-7G3, or ChAcNLS21-7G3 at short time points or in (B) exposed to filipin prior to incubation are shown.
Figure 6:
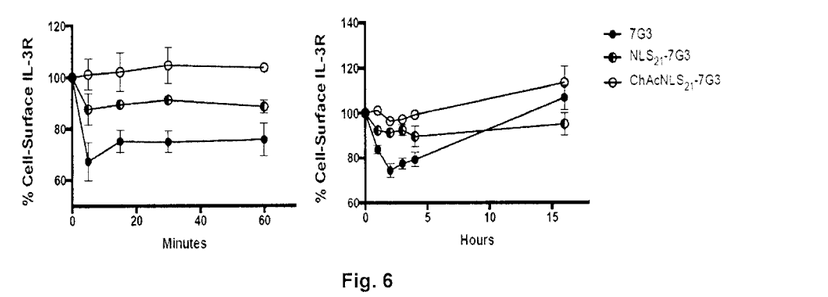
FIG. 6 illustrates the effect on IL-3Rα internalization and recycling, wherein the cell surface expression of IL-3Rα on TF-1a cells was evaluated with PE-Cy7-anti-IL-3Rα antibody (clone 6H6) after incubation with 7G3, NLS21-7G3, or ChAcNLS21-7G3 at early (left panel) and late (right panel) time points, and wherein relative 7G3 presence was calculated as the geometric mean intensity of fluorescence normalized to cells incubated only in fresh medium.

Accordingly, it is provided in an embodiment, a novel cholic acid (ChAc)-NLS fusion peptide (ChAcNLS) conjugated to 7G3 (FIG. 1A), which functionalizes this complex to escape endosome entrapment and route to and utilize the nucleus as a reservoir to enhance intracellular accumulation. Although it is known for a long time that bile acids have detergent properties for dietary lipids and facilitate intestinal absorption of these lipids, they have never been adapted for targeted disruption of cellular membranes. It is demonstrated herein that ChAcNLS can confer to mAbs (such as for example 7G3 and 6G7, but not limited to) the ability to manipulate receptor-mediated internalization to effectively escape endosome entrapment and degradation in a cell specific manner. Importantly, accumulations inside the nucleus are converted to a reservoir for increasing total intracellular accumulation. Lastly, when ChAcNLS is conjugated to a mAb and the complex radiolabeled with copper-64 ($^{64}Cu$) and injected in vivo, the amount of radioactivity delivered to a tumor for example is superior to versions that cannot escape endosome entrapment. As further seen in FIGS. 9-11, not only is ChAcNLS's ability to change enhance intracellular accumulation of an antibody clearly established but ChAcNLS does not affect the antibody's affinity and selectivity.

In general, the attachment of ChAcNLS to mAbs can be controlled. For example, protein band mobility shifts on SDS-PAGE gels were used to determine the number of peptides per antibody. The heavy chain of 7G3 migrated at the expected 50 kDa±2 kDa. 7G3 reacted with 50-fold molar excess of sulfo-SMCC resulted in 8.5±1.8 and 2.6±0.6 ChAcNLS peptides per heavy chain (FIG. 1B) and light chain of 7G3 (ChAcNLS21-7G3), respectively. At 25:1 sulfo- SMCC:7G3 ratios, ChAcNLS peptides were incorporated into 7G3 at 4.3±1.0 and 1.9±0.6 peptides per heavy and light chains (ChAcNLS12-7G3), respectively. Sulfo-SMCC: 7G3 ratios of 10:1 resulted in the conjugation of 3.5±1.5 ChAcNLS per 7G3 (ChAcNLS3-7G3). The number of reference NLS peptides per 7G3 was matched so that reference NLS-7G3 conjugates was also produced.

ChAcNLS21-7G3 could localize inside a higher proportion of TF-1a nuclei compared to 7G3 and NLS21-7G3. The average proportion of positive nuclei of TF-1a cells exposed to ChAcNLS21-7G3 was increased by a factor of 3.6 and 12.7 compared to NLS21-7G3 and 7G3, respectively ($p\leq0.0001$; FIG. 2A). The proportion of AF647 positive nuclei was 60.3±6.7, 17.0±1.7, and 5.0±3.0 per 100 nuclei for ChAcNLS21-7G3, NLS21-7G3, and 7G3, respectively. Conversely, treatment of IL-3Rα-negative Raji cells with ChAcNLS21-7G3 produced <2-3% increase in the number of positive nuclei relative to NLS21-7G3 and 7G3. These results indicate that ChAcNLS21-7G3 improves nuclear translocation specifically in TF-1a cells (FIG. 2B).

All ChAcNLS-7G3 conjugates with either 3, 12, or 21 ChAcNLS peptides per antibody could increase their nuclear accumulation by at least a factor of three (FIG. 3A; $p\leq0.05$) relative to their matched NLS-7G3 counterpart. ChAcNLS21-7G3 also had >3-fold higher nuclear accumulation compared to ChAcNLS21-mlgG2a ($p\leq0.0001$). ChAcNLS21-7G3 accumulated by a factor of 25 times higher inside the nucleus of TF-1a cells relative to unmodified 7G3. Testing in IL-3Rα-negative Raji cells produced no appreciable increase in nuclear accumulation compared to ChAcNLS21-7G3 and 7G3 (FIG. 3B). NLS21-7G3 and ChAcNLS21-mlgG2a accumulate by a factor of ~5.0 higher inside the nucleus of TF-1a cells relative to unmodified 7G3 and mlgG2a. Western Blot on isolated nuclei also revealed an increased amount of 7G3 protein in TF-1a cells treated with ChAcNLS21-7G3 by a factor of >5 relative to 7G3 and NLS21-7G3 ($p\leq0.05$; FIG. 3C). The nuclei from these cells were negative for Lamp 1 indicating the increased ChAcNLS21-7G3 accumulation inside the nucleus was not contaminated with 7G3 antibodies on the plasma membrane or within late-endosomes or lysosomes (FIG. 3D).

The treatment of TF-1a cells with ChAcNLS21-7G3 increased the proportion of cells positive for intracellular AF647 by a factor of 3.1 and 1.7 relative to 7G3 and NLS21-7G3, respectively (FIG. 4A; $p\leq0.0001$). When compared to isotype control IgG2a and NLS21-IgG2a, ChAcNLS21-7G3 improved its intracellular accumulation by a factor of 8.6 and 1.6 respectively ($p\leq0.001$). Moreover, the intracellular AF647 fluorescence intensity per cell was visually superior in TF-1a cells treated with NLS21-7G3 compared to reduced fluorescence intensities produced from the other antibody-conjugates (FIG. 4A). The increase in the average MFI over cells incubated with secondary AF647 only was 26% and 38% with 7G3 and NLS21-7G3, respectively. Whereas the intracellular MFI increased by 69% in cells treated with ChAcNLS21-7G3 (FIG. 4B).

Western Blot revealed an increased amount of 7G3 in TF-1a cells treated with ChAcNLS21-7G3 by a factor of 4.1 and 3.1 relative to 7G3 and NLS21-7G3, respectively ($p\leq0.05$; FIG. 4C). For total cell uptake, the total MFI level (nuclear-cytoplasm-cell surface) from cells incubated with ChAcNLS21-7G3 was also superior relative to 7G3 and NLS21-7G3 (FIG. 4D; $p\leq0.05$). MFI levels of TF-1a cells exposed to unmodified 7G3 increased by 52% relative to untreated cells stained with secondary AF647 only. However, NLS21-7G3 resulted in no improvement over 7G3. Conversely, ChAcNLS21-7G3 treatment of TF-1a cells produced a 77% increase relative to untreated TF-1a cells and further supports a central role for cholic acid for producing a delivery link between endosome escape and nuclear accumulation, which results in an enhancement in total cell uptake. In addition, treatment of fixed and permeabilized TF-1a cells with ChAcNLS21-7G3 resulted in binding only to IL-3Rα on the cell surface (FIG. 4D right panel). Also, given the propensity of charged peptides to accumulate in the nucleus of fixed cells independent of their trafficking, these results support ChAcNLS21-7G3 possess highly IL-3Rα-specific cellular accumulation.

The internalization dynamics in TF-1a cells treated with ChAcNLS21-7G3 was divergent from 7G3 and NLS21-7G3 conjugates and provide mechanistic insight for how ChAcNLS enhances its cellular accumulation. As expected, the % of 7G3 on the surface of TF-1a cells rapidly decreased from 125.2%±9.1% at min 5 to 42.3%±6.5% at min 60 (FIG. 5A). A similar pattern of immunoconjugate metabolism was also observed for NLS21-7G3 and ChAcNLS21-7G3. TF-1a cells exposed to 7G3 conjugates for long periods also resulted in a steady decline of 7G3, NLS21-7G3, and ChAcNLS21-7G3 on the surface of TF-1a cells. However, when TF-1a cells were preincubated with filipin, a stark difference was observed in the % surface levels of the antibody conjugates (FIG. 5B). The % of 7G3 on the surface of TF-1a cells decreased from 97.2%±1.9% to 68.4%±12.1% from minute 5 to minute 10. The % of NLS21-7G3 also decreased in a time dependent manner. However, the amount of ChAcNLS21-7G3 remained relatively stable throughout all time points reaching a maximum of 116.9%±8.2% at 5 min and a minimum of 97.6%±2.8% at 60 min.

ChAc-mediated endosome escape also caused a change in the IL-3Rα recycling pattern. There are three distinct levels of IL-3Rα on the surface of TF-1a cells after incubation with 7G3, NLS21-7G3, or ChAcNLS21-7G3 (FIG. 6). Binding by 7G3 and NLS21-7G3 caused the % of IL-3Rα to decrease to 67.3%±15.2% and 85.4%±13.4% in the first five minutes, respectively. IL-3Rα levels stabilized at ~75% and ~90%, respectively, from 10 to 60 minutes. In contrast, incubation of TF-1a cells with ChAcNLS21-7G3 resulted in ~100% of IL-3Rα present on the cell surface out to 60 minutes. At longer time points of 1-4 hours post incubation, the % of cell surface IL-3Rα remained higher in cells treated with ChAcNLS21-7G3 (FIG. 6). However, by 16 hours post incubation the level of cell surface IL-3Rα increases in TF-1a cells exposed to all 7G3 conjugates. FIG. 5 showed that all 7G3 conjugates are internalized and ChAcNLS21-7G3 internalization occurs via a cholesterol dependent mechanism. However, the presence of IL-3Rα on the cell surface remained unchanged after binding by ChAcNLS21-7G3 (FIG. 6) means that ChAcNLS induces a switch in intracellular trafficking dynamics. This switch appears to promote recycling rather than degradation.

Figure 7:
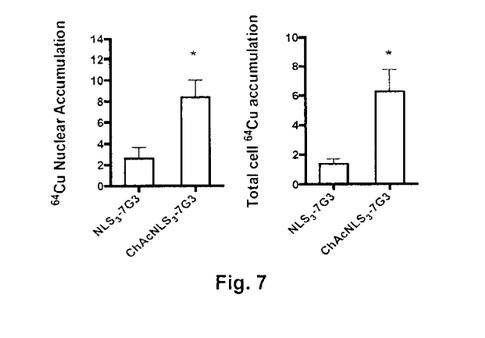
FIG. 7 illustrates $^{64}$Cu-ChAcNLS3-7G3 accumulates radioactivity in TF-1a cells, wherein the relative increase in radioactivity delivered by $^{64}$Cu-ChAcNLS3-7G3 and $^{64}$Cu-NLS3-7G3 into the nucleus (left) and total cell (right) normalized to the amount of radioactivity delivered by $^{64}$Cu-7G3 is shown.

$^{64}$Cu-ChAcNLS3-7G3 can deliver radioactivity to the nucleus of TF-1a cells more effectively than $^{64}$Cu-7G3 and $^{64}$Cu-NLS3-7G3. Moreover, the total cellular uptake of radioactivity was proportional to nuclear radioactivity accumulation. The radioactivity delivered to the nuclei of TF-1a cells by $^{64}$Cu-ChAcNLS3-7G3 was increased by a factor of 8.4 and 3.2 relative to $^{64}$Cu-7G3 and $^{64}$Cu-NLS3-7G3, respectively (FIG. 7; p≤0.001). The total radioactive uptake of $^{64}$Cu-ChAcNLS3-7G3 was increased by a factor of 5.9 and 4.3 relative to $^{64}$Cu-7G3 and $^{64}$Cu-NLS3-7G3, respectively (FIG. 7; p≤0.001). It is thus demonstrated the ability of ChAcNLS21-7G3 to accumulate in the nucleus as a reservoir to increase its total cell uptake, and that it can also deliver attached cargo (i.e. $^{64}$Cu) and increase the radioactivity into the nucleus that becomes a reservoir for increased total cellular radioactive uptake.

Figure 2A:
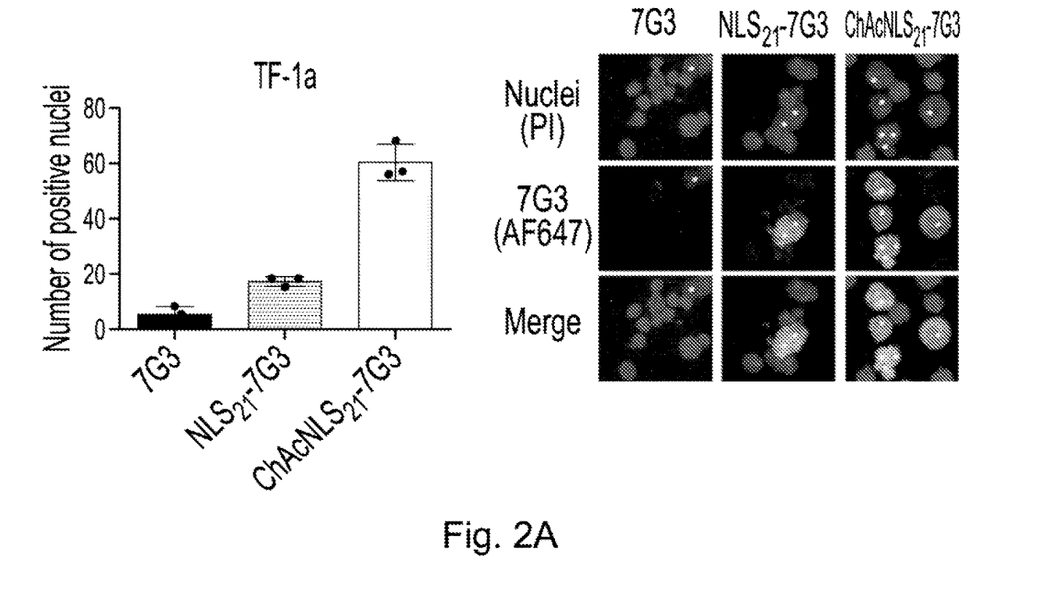
FIG. 2 illustrates the nuclear translocation of ChAcNLS21-7G3 in (A) TF-1a and in (B) Raji cells exposed to 7G3, NLS21-7G3, or ChAcNLS21-7G3, wherein the significance is indicated by black asterisk and the corresponding confocal microscopy images of isolated nuclei, stained with propidium iodide (PI), anti-murine-Fc-AlexaFluor 647 (anti-mFc-AF647) and merged are also shown, wherein nuclei with antibody accumulation are indicated by white asterisks directly on images.
Figure 2B:
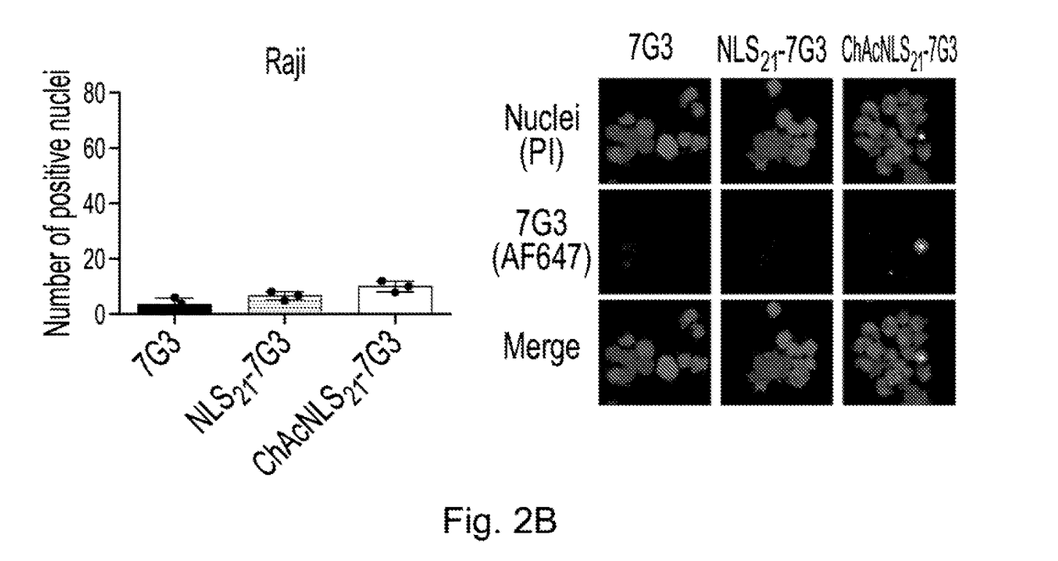
Figure 3:
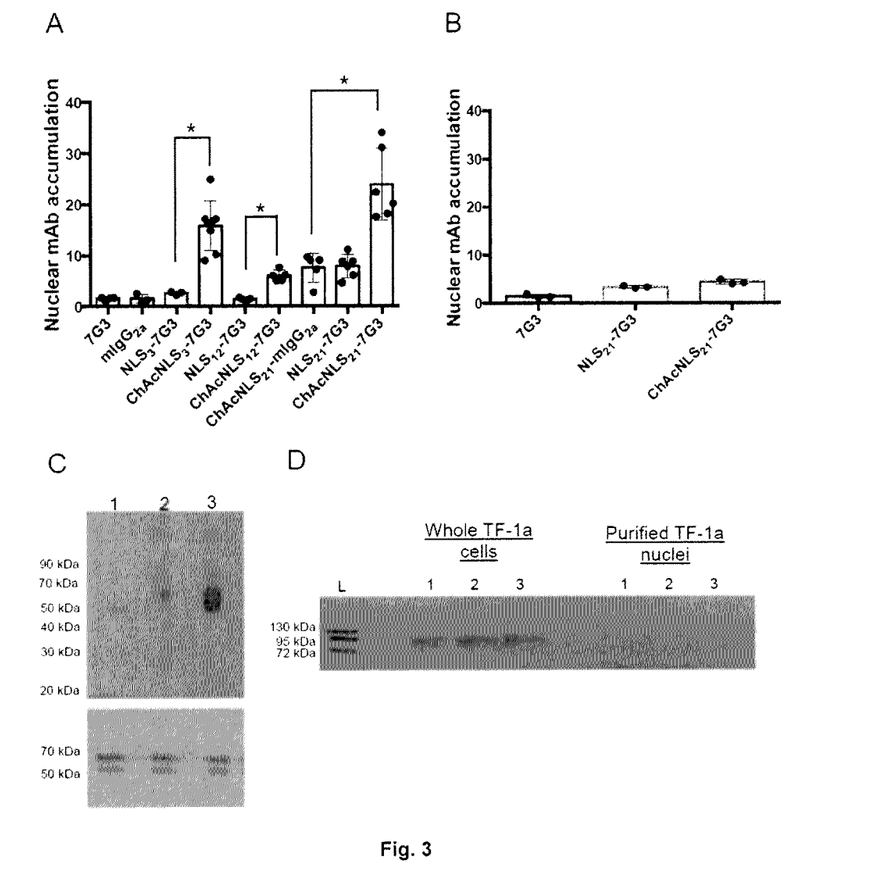
FIG. 3 illustrates the nuclear accumulation of the tested compounds, wherein mean fluorescence intensity (MFI) was measured in nuclei from (A) TF-1a and (B) Raji cells exposed to 7G3 and mIgG2a immunoconjugates, and for (C) Western Blots, isolated nuclear lysates from TF-1a cells incubated with 7G3 (lane 1), NLS21-7G3 (lane 2), or ChAcNLS21-7G3 (lane 3) are probed with anti-murine Fc antibodies (top) or anti-laminin (bottom) or stained with (D) the nuclear marker Lamp 1, wherein lysates from whole TF-1a cells challenged with the immunoconjugates are also probed for Lamp-1.

It is thus disclosed a novel peptide ChAcNLS, which is constructed by the addition of a cholic acid onto a short 13 amino acid peptide harboring a classical nuclear localization sequence. ChAcNLS is easily synthesized, water soluble, can be conjugated at low and high numbers per antibody, and does not cause unwanted aggregation. ChAcNLS-7G3 has the ability to translocate and accumulate inside the nucleus of TF-1a cells in superior quantities compared to unmodified 7G3 and NLS-7G3. Importantly, treatment of IL-3Rα-negative cells with ChAcNLS-7G3 showed nuclear translocation and accumulation levels similar to 7G3 background levels (FIGS. 2B and 3B). All ChAcNLS-7G3 conjugates attached with either 3, 12, or 21 ChAcNLS peptides have significantly higher nuclear accumulation compared to unmodified 7G3 or NLS-matched 7G3 conjugates. Furthermore, the drug delivery action of ChAcNLS3-7G3 was demonstrated with the delivery of $^{64}$Cu, which converted the nucleus into a radioactivity reservoir and enhanced total cellular accumulation of $^{64}$Cu. Accordingly, ChAcNLS is potent for functionalizing for example 7G3 to escape endosome entrapment and specifically translocate and accumulate attached cargo inside the nucleus of TF-1a cells for example.

The addition of ChAcNLS to 7G3 caused an alteration in IL-3Rα internalization and recycling dynamics relative to unmodified 7G3 and NLS-modified 7G3. Approximately 100% of IL-3Rα was recycled back to the cell surface after binding to ChAcNLS-7G3. Conversely, the % of cell-surface IL-3Rα was reduced at early time points after binding to NLS21-7G3 and 7G3. By 16 hours post incubation the original levels of cell surface IL-3Rα returned, which was most likely due to the endogenous re-expression of IL-3Rα. Importantly, IL-3Rα recycling may be an additional cause of increase cellular uptake as the availability of IL-3Rα may not be a limiting factor at least during early periods of binding. A block was observed in ChAcNLS21-7G3 when TF-1a cells were pre-exposed to filipin. In contrast, internalization of 7G3 and NLS21-7G3 was not blocked by filipin. This suggests that ChAcNLS21-7G3 internalization occurs through a cholesterol-dependent mechanism.

Figure 4:
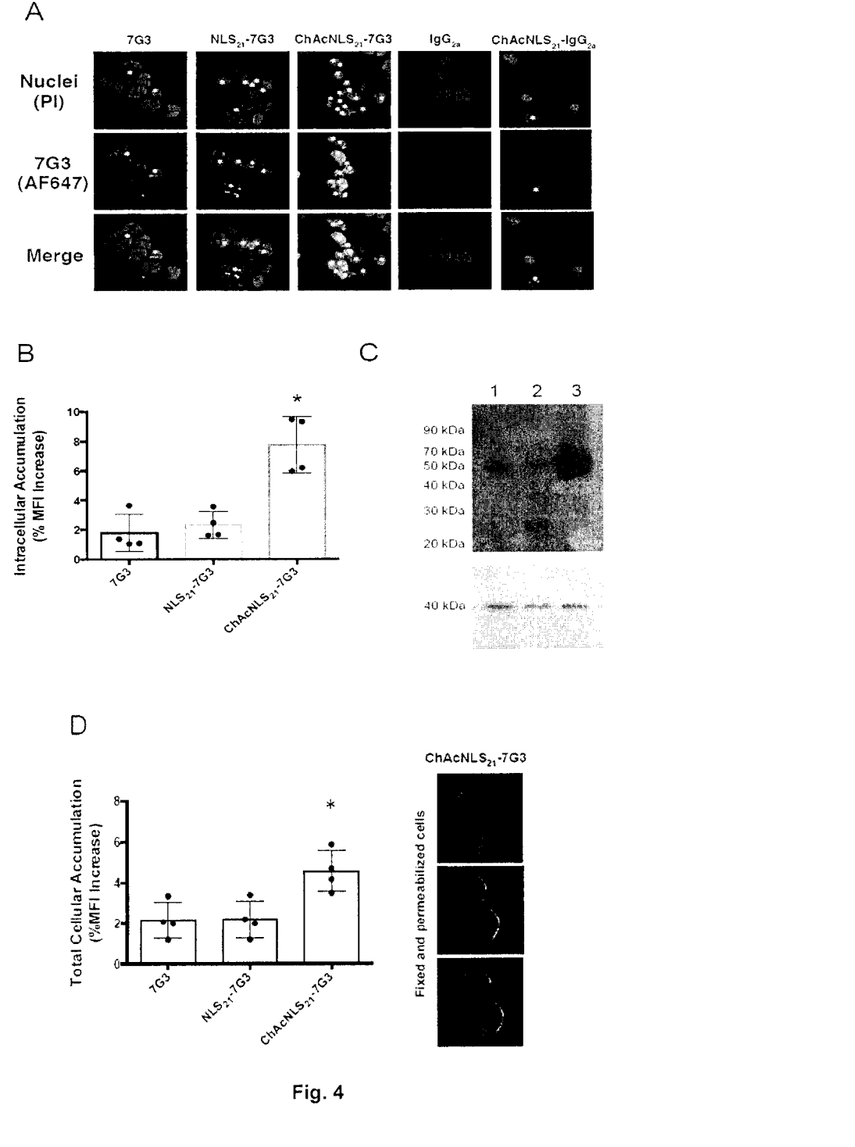
FIG. 4 illustrates intracellular and total cell accumulation of ChAcNLS21-7G3, showing in (A) confocal microscopy images of trypsinized TF-1a cells exposed to antibody-conjugates and stained with PI, anti-mFc-AF647 and merged, wherein positive intracellular accumulation is indicated by white asterisks directly on images; in (B) % intracellular MFI increase of TF-1a cells incubated with 7G3, NLS21-7G3, or ChAcNLS21-7G3 relative to cells stained with AF647 only; in (C) Western Blot of trypsinized total TF-1a cells incubated with 7G3 (lane 1), NLS21-7G3 (lane 2), or ChAcNLS21-7G3 (lane 3), wherein below is stain for actin; and in (D) total cellular MFI levels of TF-1a cells exposed to 7G3, NLS21-7G3, or ChAcNLS21-7G3, wherein significance is indicated by asterisk.

It is provided herein that ChAcNLS21-7G3 has the ability to enhance its own total cellular uptake by a factor of 2.2 relative to 7G3 and NLS21-7G3 (FIG. 4D). ChAcNLS3-7G3 also is able to transport and accumulate more $^{64}$Cu compared to 7G3 and NLS3-7G3 by a factor of 5.9 and 4.3, respectively (FIG. 7).

It is also described the ability of $^{64}$Cu-ChAcNLS3-7G3 to enhance the cellular uptake of $^{64}$Cu. Thus ChAcNLS should not disrupt the in vivo pharmacokinetics of antibodies. The conjugated compounds provided herein can lead to more effective radiotoxicity or higher sensitive detection of cancer cells because of the observed increases in radioactive retention as shown herein in tumors.

Figure 8:
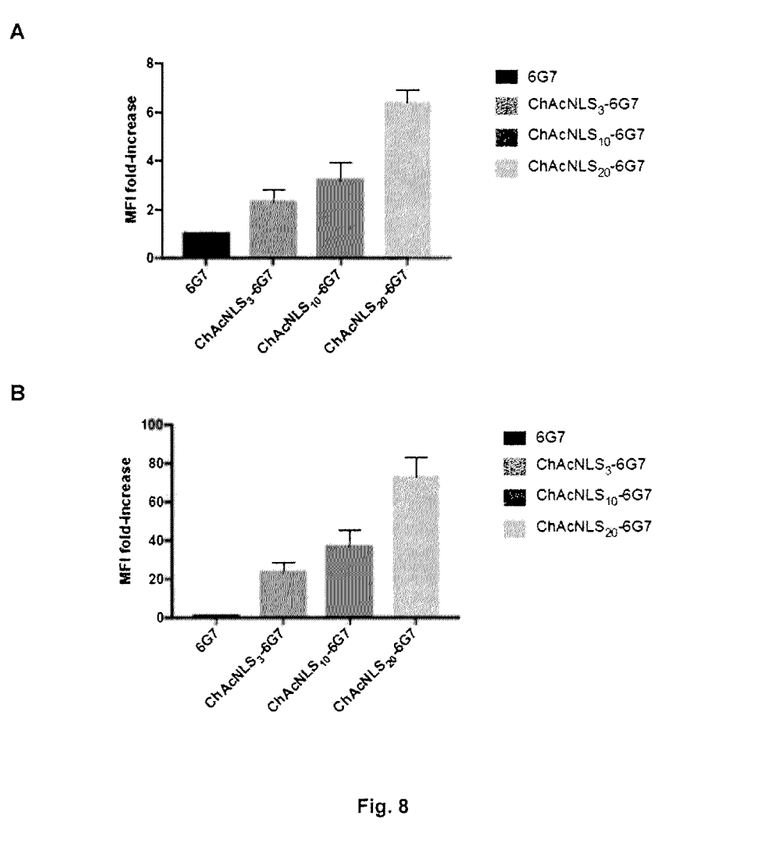
FIG. 8 illustrates the nuclear and cellular accumulation of the mAb 6G7 when functionalized with ChAcNLS at increasing amounts of ChAcNLS per 6G7, accumulation compared to unmodified 6G7, wherein in (A) ChAcNLS3-6G7 nuclear accumulation is seen and in (B) the total cellular accumulation is seen compared to unconjugated antibody measured by flow cytometry.
Figure 9:
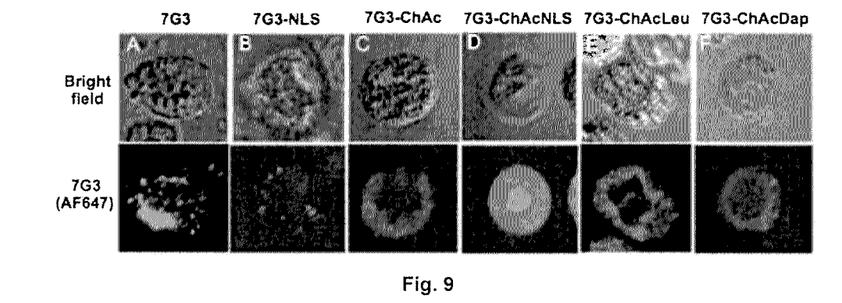
FIG. 9 illustrates cellular localization pattern of conjugated and unconjugated 7G3 antibody.
Figure 10:
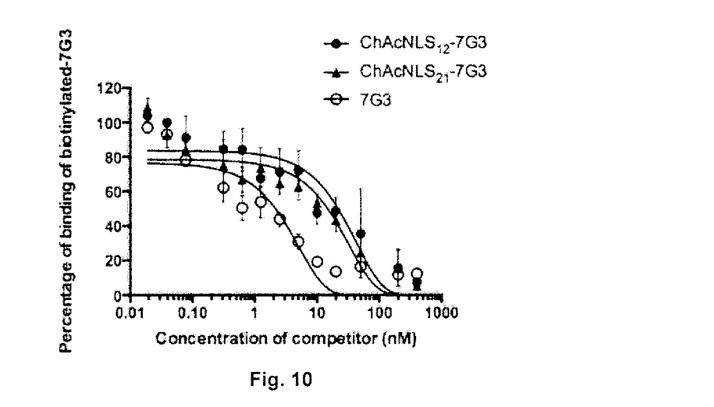
FIG. 10 illustrates binding to IL-3Rα of conjugated and unconjugated 7G3 antibody.
Figure 11:
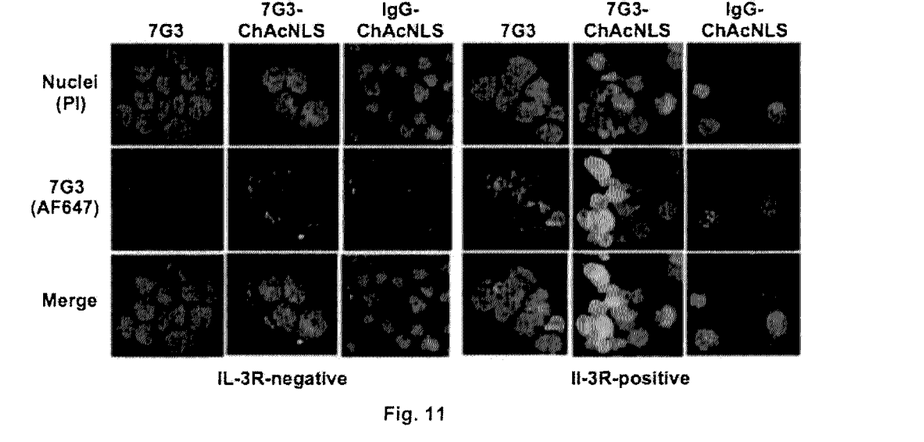
FIG. 11 illustrates immunofluorescence tracking of unconjugated 7G3 antibody in CD123-negative and positive leukemia cells.

It is thus provided a way to widely adapt other molecule or antibody by targeting rapidly internalizing receptors. Many interleukin receptors implicated in a variety of cancers undergo rapid endocytosis upon ligand binding. For example, it was demonstrated in FIG. 8 the nuclear accumulation of a conjugated antibody as encompassed herein, mainly a 6G7 leukemia antibody (ChAcNLS3-6G7). The use of a conjugate as described herein can increase accumulation of actual chemotherapeutic molecule for example in targeted cells.

In an embodiment, the antibody-drug conjugates (ADCs) as described herein are composed of three components—a monoclonal antibody (mAb), cross-linker, and a cytotoxin (e.g. small molecule chemotherapeutic). For example, the cytotoxin is conjugated to the mAb via the cross-linker. The cross-linker is typically attached to mAb surface lysines.

It is encompassed herein that the antibody-drug conjugates (ADCs) as described herein comprises a small molecule toxin such as for example and not limited to, microtubule disrupting agents (such as vinblastine, Monomethyl auristatin E or MMAE, DM1) and/or DNA alkylating agents.

For example, an antibody conjugated with ChAcNLS together with an attached chemotherapeutic molecule such as 4,4-difluoro-8-(4-carboxyphenyl)-1,3,5,7-tetramethyl-4-bora-3a,4a-diaza-s-indacene (BODIPY for short), which is a cytotoxic molecule used in photodynamic therapy applications in cancer, results in an increase cytoplasmic accumulation of the antibody and chemotherapeutic molecule since ChAcNLS does not interfere with tumor targeting, provides faster blood clearance and at the same time better tumor uptake.

Various HER2-positive cancer cells were treated with increasing concentrations of T-DM1 and ChAcNLS-T-DM1 for 72 h. Cytotoxicity was measured using Alamar Blue®, which measures cell proliferation. T-DM1 is a chemotherapeutic, also known as emtansine (trastuzumab-DM1) marketed as Kadcyla® (Roche). The cells and their specific cancer, level of HER2 expression, and resistance status are described as follows:

TABLE 1

Cells specifications

| Cells | Cancer | HER2 status | Herceptin-resistant |
|---|---|---|---|
| SKBR3 | Breast | 1 × 10$^6$ (100%) | No |
| OE19 | Ovarian | 69.7% | No |
| JIMT1 | Breast | 56.4% | Yes |
| MCF7 | Breast | Negative | — |

Figure 14:
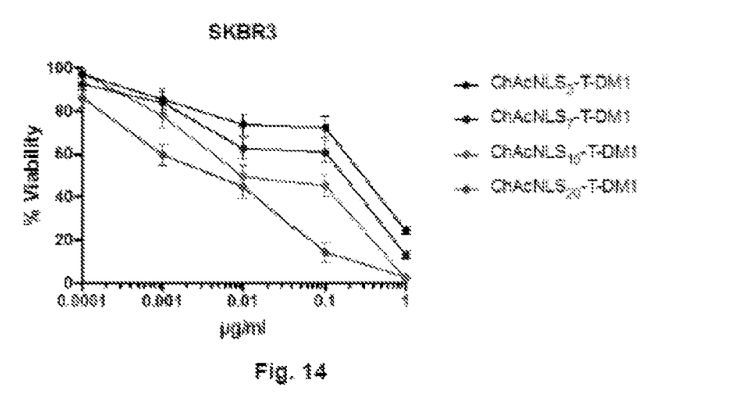
FIG. 14 illustrates T-DM1 conjugated with ChAcNLS via the MCC cross-linker displayed dose-dependent killing with increasing ADC concentration and with increasing number of ChAcNLS per T-DM1, SKBR cells that express very high levels of Her2 were used for this demonstration.

As seen in FIG. 14, it is demonstrated that ChAcNLS-T-DM1 has dose dependent killing both with increasing concentration of ChAcNLS-T-DM1 with increasing amounts of ChAcNLS per T-DM1.

Figure 15:
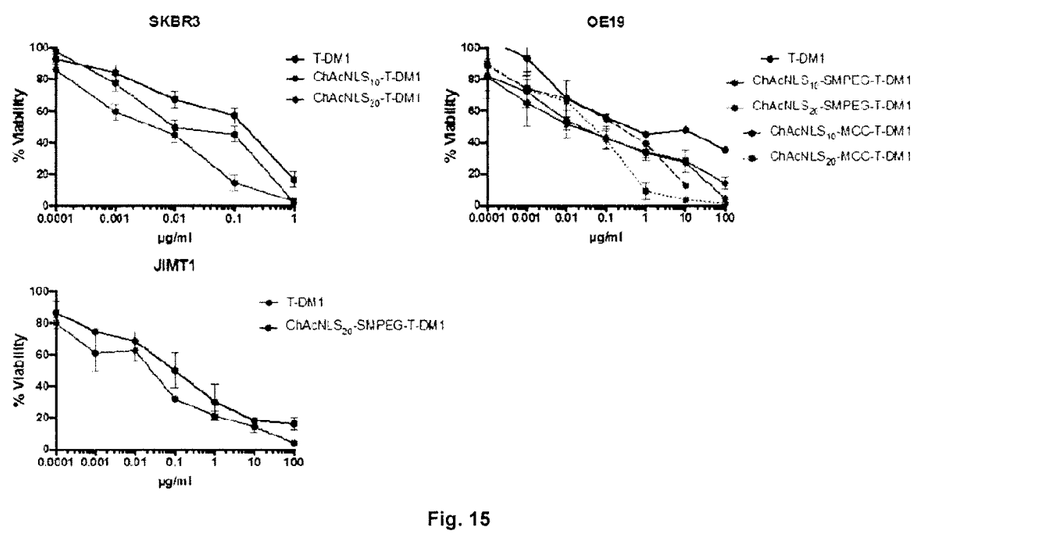
FIG. 15 illustrates the $IC_{50}$ of ChAcNLS-T-DM1 increased by 100-, 50, and 10-fold relative to T-DM1 in SKBR3, OE19, and JIMT1 cells, respectively.

FIG. 15 depicts the improved cytotoxicity profiles for ChAcNLS-T-DM1 relative to T-DM1 in the Herceptin-sensitive cell line SKBR3 and in two Herceptin-resistant cell lines OE19 and JIMT1.

Figure 16:
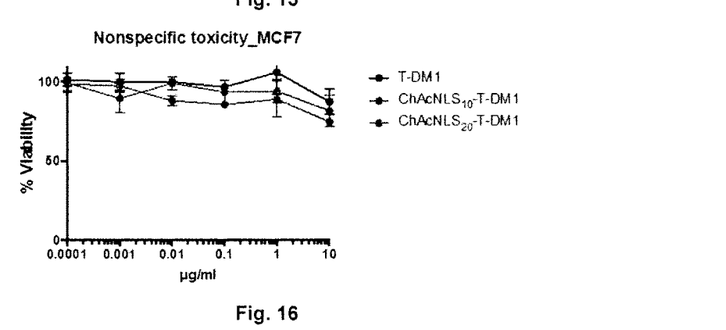
FIG. 16 illustrates that in Her2-negative breast cancer cell line MCF7, ChAcNLS-T-DM1 does not display unwanted cytotoxicity against cells that do not express the target.

In Her2-negative breast cancer cell line MCF7, ChAcNLS-T-DM1 does not display unwanted cytotoxicity against cells that do not express the target (FIG. 16).

Acute and embryonic nonspecific toxicity was evaluated in 13 day old chicken embryos ex ovo. One and 10 µg/chick of ChAcNLS-SM(PEG)2-T-DM1 and ChAcNLS-MCC-T-DM1 (loaded with 20 ChAcNLS/antibody) were intravenously injected and evaluated for survival for 72 h. Equivalent doses of T-DM1 were also injected and evaluated for comparison. Results are depicted in Table 2.

TABLE 2

| | Number of chicks alive after 72 h | |
|---|---|---|
| PBS negative ctrl | 2 out of 2 survived | |
| Drug | 0.1 µg | 1 µg |
| T-DM1 | 4/4 | 4/4 |
| ChAcNLS-MCC-T-DM1 | 2/2 | 1/2 |
| ChAcNLS-PEG-T-DM1 | 3/3 | 4/4 |

Both formulations of ChAcNLS-T-DM1 have no acute toxicity on embryonic chickens.

Not only the conjugate as described herein provides a mean to enhance delivery of an antibody, but ChAcNLS can enhance the delivery of an attached molecular payload, not just the antibody. ChAcNLS can deliver increased amounts of a molecular payload to the nucleus.

Figure 12:
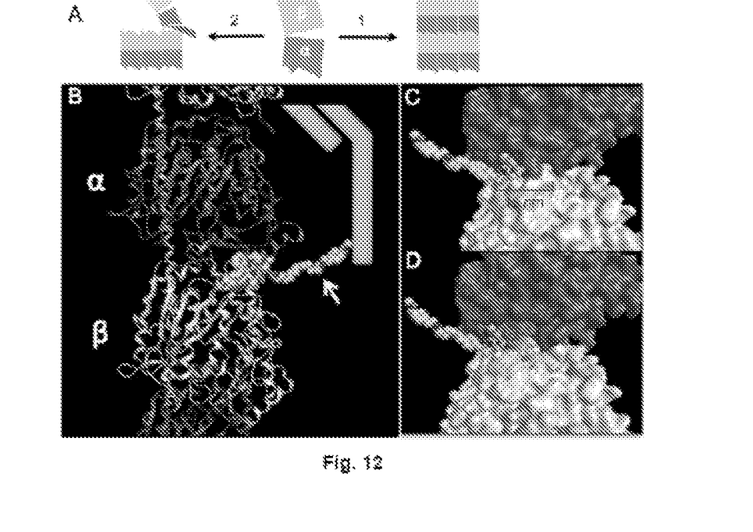
FIG. 12 illustrates a structure-guided analysis for vinAC design, showing in (A) molecular mechanism of action of vinblasline; (B) side view of protein secondary structure of α- and β-tubulin monomers with vinblastine-C10-SMCC wedge; (C) vinblasline inserted in the 15 nm binding pocket; and (D) residues from α- and β-tubulin blocking vinblastine docking are removed.
Figure 13:
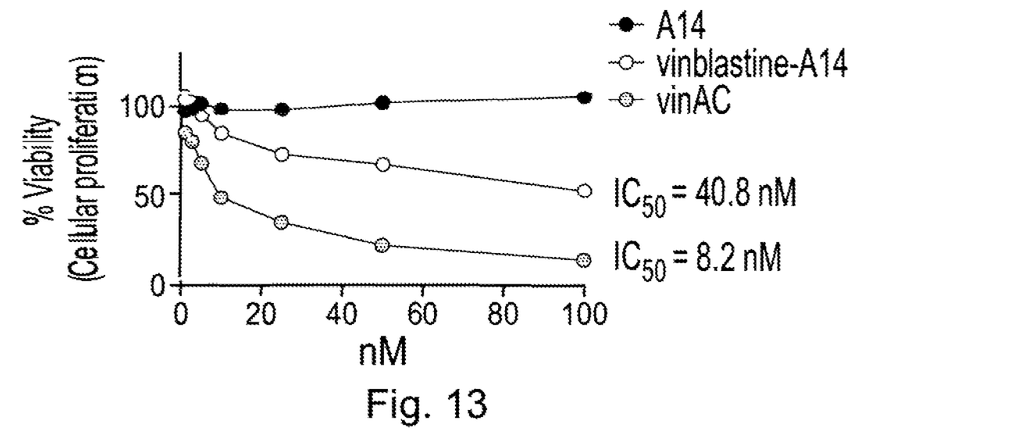
FIG. 13 illustrates % of MIBC cell viability determined by XTT cellular proliferation assay, cell treated with VinAC generated from the reaction with vinblastine and ChAcNLS.

It is further encompassed herein the possibility of not only conjugated an antibody as described herein but also conjugating the antibody with a further drug, such as vinblastine, which is used in combination with other chemotherapy drugs to treat Hodgkin's lymphoma (Hodgkin's disease) and non-Hodgkin's lymphoma, and cancer of the testicles. It is also used to treat Langerhans cell histiocytosis. As seen in FIG. 12A, in the absence of vinblastine, curved αβ-tubulin heterodimers assemble into microtubules and undergo a curved-to-straight conformational transition. Vinblastine binds to its inhibition site, a composite site that is formed by structural elements from both α- and β-tubulin monomers. Vinblastine destabilizes microtubules by introducing a wedge preventing the curved-to-straight conformational transition necessary to build up the microtubule lattice. It is disclosed an antibody-drug-conjugate with ChAcNLS. As demonstrated, ChAcNLS can make the antibody-drug-conjugate 5-fold more toxic than standard antibody-drug conjugate.

Accordingly, the conjugated compound described herein can be used for detecting or treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia or colorectal cancer.

The present disclosure will be more readily understood by referring to the following examples which are given to illustrate embodiments rather than to limit its scope.

Example I

ChAcNLS-7G3 Construction

ChAcNLS was designed with the nuclear localization sequence from SV-40 large T antigen with GYG and GG spacer residues at the N- and C-terminus, respectively. The N-terminus was capped with a cysteine for conjugation to ChAc and 7G3. ChAcNLS and NLS were conjugated to 7G3 or mIgG2a mAbs by reaction of maleimide-derivatized 7G3 with the N-terminal cysteine of the ChAcNLS. Maleimide groups were introduced into 7G3 by reaction of 10 mg/mL 7G3 in PBS, pH 7.6, with 10-, 25-, or 50-fold molar excess of sulfosuccinimidyl-4-(N-maleimidomethyl)-cyclohexane-1-carboxylate (sulfo-SMCC; VWR, Quebec, Canada) at room temperature for 1 h. Maleimide-derivatized 7G3 was purified on a Sephadex G-50 (Sigma-Aldrich) column eluted with PBS, pH 7.0. Fractions containing maleimide-7G3 were transferred to a Centricon YM-100 ultrafiltration device (EMD Millipore, Ontario, Canada) and concentrated to 10 mg/mL, which was then reacted with 100-fold molar excess of ChAcNLS for 18 h at 4° C. ChAcNLS-7G3 was purified from excess ChAcNLS and concentrated in PBS, pH 7.4, by ultrafiltration through a Centricon-YM-100.

Example II

Exposure of Cells to mAb Conjugates

TF-1a leukemia and Raji Burkitt's lymphoma cells were obtained from the American Type Tissue Collection (Manassas, Va.). TF-1a cells are positive for IL-3Rα by flow cytometry (corresponding to $7.8 \times 10^3$ receptors/cell for $^{111}$In-labeled chimeric version of 7G3, and Raji cells are IL-3Rα-negative. Cells were cultured in RPMI 1640 medium supplemented with 1% penicillin/streptomycin, 1% non-essential amino acids, 1% sodium pyruvate, 10% heat inactivated FBS, and 0.2% amphotericin B (Wisent, Quebec, Canada).

$5 \times 10^6$ TF-1a cells were exposed to 200 nmol/L of 7G3 or mIgG2a conjugates in RPMI/10% FBS for 1 h at 37° C. Cells were then washed 3× in ice-cold PBS and suspended in RPMI/10% FBS for an additional 1 h at 37° C. as a post-incubation. This allowed for the evaluation of internalization and intracellular accumulation of the antibody-conjugates to be monitored by the methods utilized in this study. Cells were then centrifuged and washed in ice-cold PBS.

To isolate the cell nuclei, TF-1a cells were washed in ice-cold PBS and then lysed by suspending in 0.05% NP-40, 10 mmol/L Tris pH 7.5, 10 mmol/L NaCl, 3 mmol/L MgCl$_2$ buffer on ice for 10 min. Lysed cells were then centrifuged at 80 g for 5 min. The nuclei pellet was then washed without NP-40 and centrifuged at 80 g for an additional 5 min. Nuclei were washed 3× in ice cold PBS. Isolated nuclei were lysed in RIPA buffer. Total protein concentration was determined using the BCA Protein Assay Reagent (VWR). 10 pg of protein were loaded into wells in a 12% SDS gel and electrophoresed at 180 V for 1 h. The gel was transferred on to a PVDF membrane at 100 V for 1 h. PVDF membranes were then placed into a 5% milk/TBS/0.1% Tween™ 20 blocking solution for 1 h followed by washing 3× in TBS/0.1% Tween 20. Membrane was then incubated in 2.5% milk/PBS containing 2 pg/mL of anti-murine Fc secondary polyclonal antibody conjugated to horseradish peroxidase (HRP; Life technologies) for 1 h at room temperature. HRP signal was revealed by enhanced chemiluminescence (Bio-Rad). Polyclonal rabbit antibodies against the well-established nuclear marker laminA/C (Santa Cruz Biotechnology Inc, Dallas, Tex.) and plasma membrane/late endosome/lysosomal marker Lamp 1 (Sigma-Aldrich) were used for Western Blot loading control and densitometry. LaminA/C and Lamp 1 were also controls to determine nuclei enrichment and ensure nuclei were free of contaminants from the plasma membrane, late-endosomes or lysosomes. Nuclear fractionation efficiency was also determined by flow cytometry by evaluating the changes in FSC vs SSC from intact cells to isolated nuclei. The smaller nuclei population is distinct from intact cells. Nuclei were stained with propidium iodide (PI), which binds to DNA, for 5 min prior to analysis to confirm DNA is contained in the nuclei population.

To track nuclear localization and accumulation, after incubating cells with 7G3 or mIgG$_{2a}$, followed by washing and cell fractionation steps, isolated nuclei were fixed in 1% paraformaldehyde/1% sucrose on ice for 30 min. Nuclei were then washed and suspended in 0.5 mL PBS containing 2 pg/mL of anti-murine Fc secondary polyclonal antibody conjugated to Alexa Fluor® 647 (AF647; Life technologies, Ontario, Canada) for 1 h at room temperature in the dark. Nuclei were washed and then treated with 10 pg/mL of PI 5 min prior to analysis. For confocal microscopy, isolated nuclei were mounted onto glass slides with SlowFade mounting media (Life technologies) and covered with a glass coverslip. All images were acquired on a FV1000 scanning confocal microscope (Olympus, Tokyo, Japan) coupled to an inverted microscope using a 63× oil immersion objective. PI fluorescence was detected with 488 nm argon laser and a >590 nm filter. AF647 fluorescence was detected using a 633 nm helium-neon laser and >590 nm filter. Fluorescence emissions from PI and AF647 were collected sequentially. Serial horizontal optical sections of 1024×1024 pixels with 2 times line averaging were taken at 0.5 µm intervals through the entire cell thickness. Images were acquired in the same day and pseudocolored and merged (FluoView; Olympus). The ability of the 7G3 conjugates to translocate to the nucleus was determined by the proportion of AF647 fluorescence positive nuclei. Flow cytometric evaluation was used to determine antibody-conjugate accumulation, which was calculated as the geometric mean fluorescence intensity (MFI) relative to background MFI levels in nuclei incubated with AF647 only as determined by CellQuest Pro software (BD Biosciences).

To investigate improvements by ChAcNLS-7G3 to accumulate specifically in TF-1a cells, 2×10$^6$ cells were treated under the exact same conditions. Cells were then suspended in 0.1 mL of PBS containing 0.25% Trypsin (Sigma-Aldrich) and 0.25% EDTA and incubated at 37° C. for 3 min, which was used to remove surface bound antibody-conjugates. Trypsin was neutralized with the addition of 0.4 mL of RPMI/10% FBS. Cells were then fixed. Cells were washed and then permeabilized with 0.15% Triton X™ for 5 min. Cells were then washed and suspended in PBS and stained with AF647 and PI. In addition, to control for potential non-specific trafficking activity by the positive charged peptides on fixed cells, non-treated TF-1a cells were also fixed and permeabilized. The fixed and permeabilized TF-1a cells were post treated with ChAcNLS-7G3 for 1 h at 37° C. followed by washing and staining with AF647 antibodies and PI. For total cellular uptake of ChAcNLS-7G3, the procedure was the same but without the addition of trypsin. Data was acquired by counting the proportion of AF647-positive cells by confocal microscopy. Intra- and total cellular accumulation was quantified by measuring the MFI within the intact fixed and permeabilized cell population, as determined by the forward scatter/side scatter distribution and positive PI staining.

Approximately 1.5 mg of 7G3 (5 µg/µL in 50 mM NaHCO$_3$ buffer, pH 7.5) was reacted with 1,4,7,10-tetra azacyclododecane-1,4,7,10-tetra acetic acid (DOTA; for complexing copper-64 ($^{64}$Cu)). DOTA-conjugates were purified on an Amicon Ultra centrifugal filter (Millipore). Approximately 500 µg of DOTA-conjugates were reacted with sulfo-SMCC and conjugated to ChAcNLS or NLS as previously described and then purified by centrifugation. 50 µg of DOTA-ChAcNLS-conjugates were placed in 50 µL of 0.1 M ammonium acetate, pH 5.5 for 1 h at room temperature with 8 MBq of $^{64}$CuCl$_2$. The radioimmunoconjugates were purified by dilution in PBC followed by centrifugation in Amicon centrifugal filters. Radiochemical purity was determined by instant thin layer chromatography developed in 100 mM sodium citrate, pH 5.5. The final radiochemical purity of all radioimmunoconjugates was >98%. 100 nmol/L of radioimmunoconjugates were added to 4×10$^6$ TF-1a cells and incubated. Cells were then washed and total cell radioactivity was measured in a gamma counter. Cells were then fractionated and radioactivity in isolated nuclei was also determined.

Example III

ChAcNLS-7G3 Internalization and IL-3Rα Recycling

For monitoring the fate of 7G3 and IL-3Rα at the cell surface of TF-1a cells, samples contained 24×10$^6$ cells and were exposed to 7G3 conjugates for 1 h. Cells were then washed to remove unbound ligand and a post-incubation at either early (5 min, 15 min, 30 min, 1 h) or late (1 h, 2 h, 3 h, and 4 h) time points was performed. At each time point, 4×10$^6$ cell aliquots were fixed and washed but not permeabilized. Cells were stained on ice for 1 h in PBS containing AF647 to monitor the level of 7G3 on the surface of cells or anti-IL-3Rα-PE-Cy7 mAb (clone 6H6; BDBiosciences) to monitor the surface expression of IL-3Rα. 6H6 does not interfere with 7G3. TF-1a cells were also exposed to filipin (5 µg/mL) for 30 min prior to exposure to 7G3 conjugates for 5, 10, 30, 60, and 120 min. PI negative cell populations were only evaluated to ensure only non-permeabilized cells were analyzed.

Example IV mAb Trastuzumab Conjugated to the Chemotherapeutic Emtansine

In order to construct ChAcNLS-T-DM1, initially ACCUM was cross-linked to surface lysines of trastuzumab using the same cross-linker described hereinabove.

Figure 17:
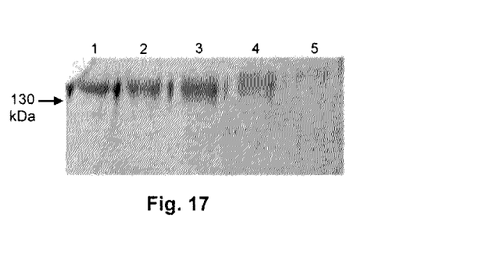
FIG. 17 illustrates on 8% non-reducing gel SDS-PAGE that increasing MCC-to-T-DM1 ratio followed by 2-molar reaction with ChAcNLS results in increasing number of ChAcNLS moieties per T-DM1, showing in lanes 1: T-DM1; 2: ChAcNLS-T-DM1 (10×MCC); 3: ChAcNLS-T-DM1 (25×MCC); 4: ChAcNLS-T-DM1 (50×MCC); and 5: ChAcNLS-T-DM1 (100×MCC).

However, there was significant aggregation of ChAcNLS-T-DM1 when reacting T-DM1 with MCC, resulting in ChAcNLS-T-DM1 increasing in size with increasing ratios of MCC-to-T-DM1 (see FIG. 17). Because MCC is hydrophobic, it is believed that a second MCC conjugation introduced excess hydrophobicity resulting in the aggregation. In order to use ChAcNLS-MCC-T-DM1, soluble monomers were purified using size-exclusion chromatography. Therefore, ChAcNLS was integrated into T-DM1 using a hydrophilic conjugation system. The crosslinker SM(PEG)$_2$ (ThermoFisher) was reacted with T-DM1 at increasing ratios and then coupled to ChAcNLS.

Figure 18:
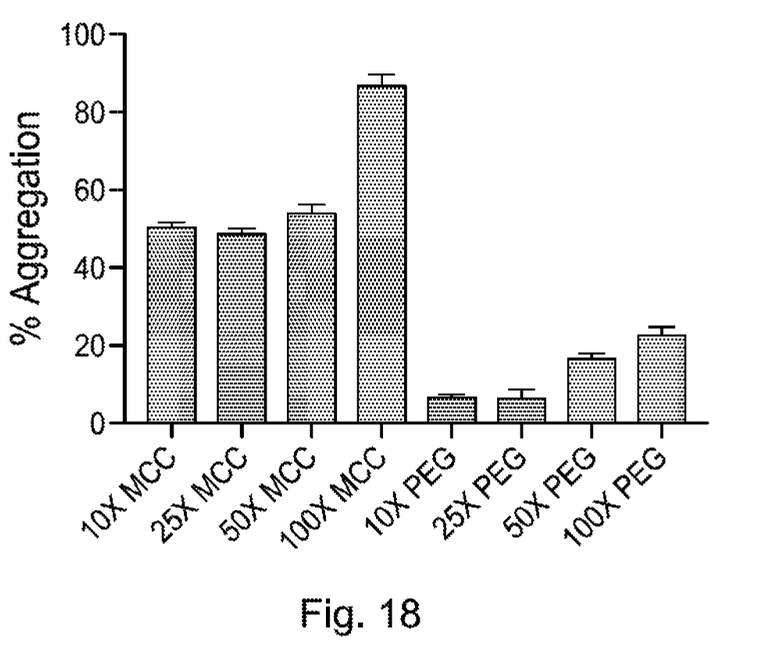
FIG. 18 is an histogram showing that SM(PEG)$_2$ conjugation eliminates unwanted aggregation of ChAcNLS-T-DM1, wherein constructs were evaluated for aggregation by UV/Vis optical density 550 nm/280 nm.

FIG. 18 shows that SM(PEG)$_2$ conjugation eliminates unwanted aggregation of ChAcNLS-T-DM1. The products were evaluated for aggregation by SDS-PAGE and precipitation by Vis/UV (550 nm/280 nm) optical density ratio. For turbidity, 550 nm measure turbidity and the 280 nm measures protein. Conjugation of ChAcNLS dramatically reduces aggregation.

While the invention has been described in connection with specific embodiments thereof, it will be understood that it is capable of further modifications and this application is intended to cover any variations, uses, or adaptations of the including such departures from the present disclosure as come within known or customary practice within the art to which the invention pertains and as may be applied to the essential features hereinbefore set forth, and as follows in the scope of the appended claims.

What is claimed is:

1. A conjugated compound consisting essentially of an antibody covalently linked to a nuclear localization sequence (NLS) as set forth in SEQ ID NO: 1, said NLS covalently linked to cholic acid (ChAc).

2. The conjugated compound of claim 1, wherein the antibody is a monoclonal or polyclonal antibody.

3. The conjugated compound of claim 1, wherein the antibody is a mouse antibody, a goat antibody, a human antibody or a rabbit antibody.

4. The conjugated compound of claim 1, wherein said antibody is a humanized antibody.

5. The conjugated compound of claim 1, wherein the antibody is the 7G3 antibody or the 6G7 antibody.

6. The conjugated compound of claim 1, wherein the ratio of ChAcNLS peptide conjugated per antibody is between 1 to 21 peptides per compound.

7. A composition comprising the conjugated compound of claim 1, a payload, and a carrier.

8. The composition of claim 7, wherein a payload is covalently linked to the antibody.

9. The composition of claim 7, wherein the payload is a radionuclide.

10. The composition of claim 9, wherein the radionuclide is at least one of $^{47}SC$, $^{51}Cr$, $^{52m}Mn$, $^{55}Co$, $^{58}Co$, $^{52}Fe$ $^{56}Ni$, $^{57}Ni$, $^{61}Cu$, $^{62}Cu$, $^{64}Cu$, $^{67}Cu$, $^{66}Ga$, $^{68}Ga$, $^{67}Ga$ $^{72}As$, $^{77}As$, $^{89}Zr$, $^{90}Y$, $^{94m}Tc$, $^{99m}Tc$, $^{97}Ru$, $^{105}Rh$, $^{109}Pd$, $^{111}Ag$, $^{110}In$, $^{111}In$, $^{113}min$, $^{114}min$, $^{117m}Sn$, $^{121}Sn$, $^{127}Te$, $^{142}Pr$, $^{143}Pr$, $^{149}Pm$, $^{151}Pm$, $^{149}Tb$, $^{153}Sm$, $^{157}Gd$, $^{161}Tb$, $^{166}Ho$, $^{165}Dy$, $^{169}Er$, $^{169}Yb$, $^{175}Yb$, $^{172}Tm$, $^{177}Lu$, $^{186}Re$, $^{188}Re$, $^{191}Pt$, $^{197}Hg$, $^{198}Au$, $^{199}Au$, $^{201}Tl$, $^{203}Pb$, $^{211}At$, $^{212}Bi$, $^{213}Bi$, $^{11}C$, $^{75}Br$, $^{76}Br$, $^{77}Br$, $^{82}Br$, $^{18}F$, $^{120}I$, $^{123}I$, $^{124}I$, $^{125}I$, $^{131}I$, $^{89}Sr$ and $^{225}Ac$.

11. The composition of claim 9, wherein the radionuclide is $^{64}Cu$.

12. The composition of claim 7, wherein the payload is a molecule toxin.

13. The composition of claim 12, wherein the molecule toxin is a chemotherapeutic agent.

14. The composition of claim 12, wherein the molecule toxin is vinblastine, emtansine, Monomethyl auristatin E or 4,4-difluoro-8-(4-carbwryphenyl)-1,3,5,7-tetramethyl-4-bora-3a,4a-diaza-s-indacene (BODIPY).

* * * * *

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Artificial Sequence
<220> FEATURE:
<223> OTHER INFORMATION: NLS  from SV-40 large T-antigen

<400> SEQUENCE: 1

Cys Gly Tyr Gly Pro Lys Lys Lys Arg Lys Val Gly Gly
1               5                   10
```